United States Patent
Ma et al.

(10) Patent No.: US 12,073,945 B2
(45) Date of Patent: Aug. 27, 2024

(54) PATIENT VENTILATOR ASYNCHRONY DETECTION

(71) Applicant: CERNER INNOVATION, INC., Kansas City, KS (US)

(72) Inventors: Nicholas Jingyi Ma, Kansas City, MO (US); Andrew Roberts, Overland Park, KS (US); Sasanka Are, Kansas City, MO (US)

(73) Assignee: Cerner Innovation, Inc., Kansas City, MO (US)

( * ) Notice: Subject to any disclaimer, the term of this patent is extended or adjusted under 35 U.S.C. 154(b) by 471 days.

(21) Appl. No.: 17/324,459

(22) Filed: May 19, 2021

(65) Prior Publication Data

US 2021/0407676 A1    Dec. 30, 2021

Related U.S. Application Data

(60) Provisional application No. 63/046,027, filed on Jun. 30, 2020.

(51) Int. Cl.
*G16H 50/20* (2018.01)
*A61M 16/00* (2006.01)
(Continued)

(52) U.S. Cl.
CPC .......... *G16H 50/20* (2018.01); *A61M 16/024* (2017.08); *G06N 20/00* (2019.01); *G16H 10/60* (2018.01);
(Continued)

(58) Field of Classification Search
CPC ........ G16H 50/20; G16H 10/60; G16H 50/30; G16H 40/40; A61M 16/024;
(Continued)

(56) References Cited

U.S. PATENT DOCUMENTS 4,960,118 A  * 10/1990  Pennock .............. A61B 5/6831
                                                      600/534
8,644,568 B1 *  2/2014  Hoffmann .............. G16H 50/50
                                                      382/128
(Continued)

FOREIGN PATENT DOCUMENTS

WO    WO-2006079152 A1 *  8/2006  ........... A61B 5/0871

OTHER PUBLICATIONS

Mcinnes et al., UMAP: Uniform Manifold Approximation and Projection for Dimension Reduction, arXiv:1802.03426 [stat.ML], https://arxiv.org/abs/1802.03426, 63 pages (Year: 2018).*

*Primary Examiner* — Jason S Tiedeman
(74) *Attorney, Agent, or Firm* — Invoke

(57) ABSTRACT

A decision support tool is provided for identifying and assisting clinicians with patient ventilator asynchrony. The information used to make the identification may include data from a patient's ventilator including the volume, flow, and pressure associated with that ventilator. At least some of this information may be used to compute one or more features for a time series of the data received for the patient. These features may be used in connection with heuristic rules and machine learning algorithms to identify instances of patient ventilator asynchrony. Based on the identification, one or more intervening actions may be initiated to reduce the impact of patient ventilator asynchrony.

31 Claims, 10 Drawing Sheets

(51) Int. Cl.
*G06N 20/00* (2019.01)
*G16H 10/60* (2018.01)
*G16H 20/40* (2018.01)
*G16H 40/20* (2018.01)
*G16H 40/67* (2018.01)
*G16H 50/30* (2018.01)
*G16H 50/70* (2018.01)
*G16H 40/40* (2018.01)

(52) U.S. Cl.
CPC ............ *G16H 20/40* (2018.01); *G16H 40/20* (2018.01); *G16H 40/67* (2018.01); *G16H 50/30* (2018.01); *G16H 50/70* (2018.01); *A61M 2016/0027* (2013.01); *A61M 2016/003* (2013.01); *A61M 2205/3379* (2013.01); *A61M 2230/42* (2013.01); *G16H 40/40* (2018.01)

(58) Field of Classification Search
CPC ...... A61M 2205/15; A61M 2205/3334; A61M 2205/52; A61M 2230/40; A61B 5/0816
See application file for complete search history.

(56) References Cited

U.S. PATENT DOCUMENTS

| | | | |
|---|---|---|---|
| 2011/0247622 A1* | 10/2011 | Schneider | A61M 16/107 |
| | | | 128/204.23 |
| 2014/0095417 A1* | 4/2014 | Herz | G16H 50/80 |
| | | | 706/12 |
| 2016/0135756 A1* | 5/2016 | Rusin | A61B 5/02055 |
| | | | 600/301 |
| 2016/0279361 A1* | 9/2016 | Mulqueeny | A61B 5/085 |
| 2017/0296767 A1* | 10/2017 | White | A61M 16/1005 |
| 2019/0167176 A1* | 6/2019 | Annoni | A61B 5/4035 |
| 2019/0167209 A1* | 6/2019 | Annoni | A61B 5/0826 |
| 2019/0371460 A1* | 12/2019 | Gutierrez | A61M 16/026 |
| 2020/0188617 A1* | 6/2020 | White | A61M 16/0051 |
| 2020/0196881 A1* | 6/2020 | Zemel | A61B 5/02444 |
| 2020/0261674 A1* | 8/2020 | Gholami | A61M 16/024 |
| 2022/0180516 A1* | 6/2022 | Mavroeidis | G06T 7/70 |
| 2022/0181023 A1* | 6/2022 | Mastoridis | G16H 50/70 |

* cited by examiner

```
###############################################################################

#      Peak Detection

###############################################################################

@njit(nogil=True)
def find_peaks(s, width=7):
    """
    Find maximum of array s, including only points which are maximal
    compared to all points within a width If minimums are desired, find maximums of -s
    """
    # change to half-width
    width = int(np.ceil((width - 1) / 2))
    mx = (np.diff(np.sign(np.diff(s))) < 0).nonzero()[0] + 1  # local max
    mx_check = np.zeros(mx.shape[0], dtype=np.bool_)
    for i in prange(mx.shape[0]):
        # if peak is greater than all points within width, set to true
        if (
            s[slice(
                mx[i] - width if mx[i] >= width else 0,
                mx[i] + width + 1
            )].max()
            == s[mx[i]]
        ):
            mx_check[i] = True
    return mx[mx_check]  # filter to points which were max within width
```

*FIG. 7A.*

```
################################################################################

#       Breath Detection

########################################################################## def wave_slice(vol, pres, width=20, minpresrange=1, minthresh=2, thresh=10):
    # look for min peaks in volume, but not if the value is too high
    wave_ex = [x for x in find_peaks(-vol.values, width=width) if vol[x] < minthresh]
    # identify gaps in the data which happen occasionally
    gaps = pd.Series(vol.index).diff() > timedelta(seconds=0.02)
    gaps = gaps[gaps].index.to_list()
    wave_ex = sorted(wave_ex + gaps)
    prev = 0
    # cut series before/after gaps
    for i in range(len(wave_ex) - 1):
      # data sometimes cuts out, want to get rid of extra point in this case
      if wave_ex[i + 1] in gaps:
        if wave_ex[i] - prev >= thresh:
          yield slice(prev, wave_ex[i] + 1)
        prev = wave_ex[i + 2]
      # we check here that enough time has passed to constitute a breath
      elif wave_ex[i] - prev >= thresh:
        # only output if pressure change has exceeded minpresrange
        if (
          pres[slice(prev, wave_ex[i] + 1)].max()
          - pres[slice(prev, wave_ex[i] + 1)].min()
          > minpresrange
        ):
          yield slice(prev, wave_ex[i] + 1)
          prev = wave_ex[i]
```

*FIG. 7B.*

```
###########################################################################

#       Asynchrony/Anonamly Group Detection

##################################################################### flow_ratio is the ratio exhalation to inhalation before the end volume drop
wave_agg.loc[wave_agg.flow_ratio < 0.6, "manual_label"] = 1
# vol_osc_ratio is the amplitude of oscillation in the volume peak
# (relative to the peak height)
wave_agg.loc[wave_agg.vol_osc_ratio > 0.25, "manual_label"] = 2
# the ratio of the time to next volume peak to the time from the previous
wave_agg.loc[wave_agg.vol_peak_time_ratio < 0.7, "manual_label"] = 3
# ratio of distances between pressure peak start times (between this-next
# and prev-this)
wave_agg.loc[wave_agg.pres_peak_time_ratio < 0.6, "manual_label"] = 4
# exhalation time divided by inhalation time
wave_agg.loc[wave_agg.time_ratio < 0.8, "manual_label"] = 5
```

*FIG. 7C.*

PATIENT VENTILATOR ASYNCHRONY DETECTION

CROSS REFERENCE

This application claims the benefit of U.S. Provisional Application No. 63/046,027 filed Jun. 30, 2020, which is incorporated herein by reference in its entirety.

BACKGROUND

Patient ventilator asynchrony is a mismatch between a mechanical ventilator and a patient receiving partial ventilator support. Asynchrony between a patient and the ventilator can have significant consequences on a patient's health and recovery time. It is a common phenomenon, with incidence rates ranging from 10% to 85%. Patient ventilation asynchrony might be due to factors related to the patient, to the ventilator, or both. This issue has been associated with unwanted outcomes, such as discomfort, dyspnea, worsening of pulmonary gas exchange, an increased work of breathing, diaphragmatic injury, sleep impairment, and increased use of sedation or neuromuscular blockade, as well as increases in the duration of mechanical ventilation, weaning time, and mortality. Currently clinicians are required to continuously monitor a patient's ventilator data to check for patient ventilator asynchrony, which may require manual evaluation of a large amount of data by an expert.

SUMMARY

Systems, methods, and computer-readable media are provided for implementing a decision support tool for the detection of asynchrony between a patient and ventilator based on data from the ventilator system. In particular, a patient ventilator asynchrony detection system is provided for identifying asynchrony in data from a ventilator that is providing partial ventilatory support. Embodiments of the disclosure described herein may provide an indication that asynchrony is detected that will represent the likely condition that there is a mismatch between the patient's respiratory system and the ventilator that is providing mechanical ventilation to the patient. The mismatch may be a mismatch of time, flow, volume, or pressure demands.

In exemplary embodiments, physiological measurements from a patient's ventilator, such as volume, pressure, and flow, are acquired over time. One or more time series may be constructed from the measurements and used to identify individual breaths. Based on the detected breaths, embodiments of this disclosure detect the likely presence of patient ventilator asynchrony within the time interval, which would indicate a need to adjust ventilator controls. The system identifies individual breaths by identifying peaks within the time series, and a plurality of features are determined from the ventilator data for each breath. A set of logic may utilized to detect asynchrony from the features determined for each detected breadth. In some embodiments, one or more set of heuristic rules are applied to the features to identify asynchrony. In further embodiments, the features for the individual breadths may be input into one or more machine learning models that are trained to predict types of asynchrony. In some embodiments, a set of heuristic rules and one or more machine learning models are both utilized. For example, a set of heuristic rules may be applied to first detect the likely presence of asynchrony, and features for breadths that are flagged as indicating likely asynchrony may be input into one or more machine learning models to predict the likelihood of particular types of asynchrony being present.

In exemplary embodiments, one or more intervening actions may be initiated based on the detection of asynchrony in the ventilator. For example, asynchrony may indicate an issue present in the settings or set-up of the patient's ventilator system and may lead to respiratory distress that would will impact the health of the patient. In this way, embodiments of this disclosure enable more accurate and timely detection of these issues causing asynchrony and lead to intervening actions to respond with proper adjustments to the ventilator system and, in some embodiments, appropriate treatment and support for a patient affected by the asynchrony. For instance, a notification may be provided with an indication that asynchrony is present in the patient's ventilator system, and in some embodiments, a recommendation to adjust the ventilator system according to which type of asynchrony is identified may be provided. Additionally, in some embodiments, the detected asynchrony is utilized to determine a treatment recommendation for the patient to reduce or counter adverse effects of the asynchrony.

BRIEF DESCRIPTION OF THE DRAWINGS

The present invention is described in detail below with reference to the attached drawing figures, wherein:

FIGS. 7A-C depict example embodiments of computer program routines in accordance with embodiments of the present disclosure.

DETAILED DESCRIPTION

Figure 1A:
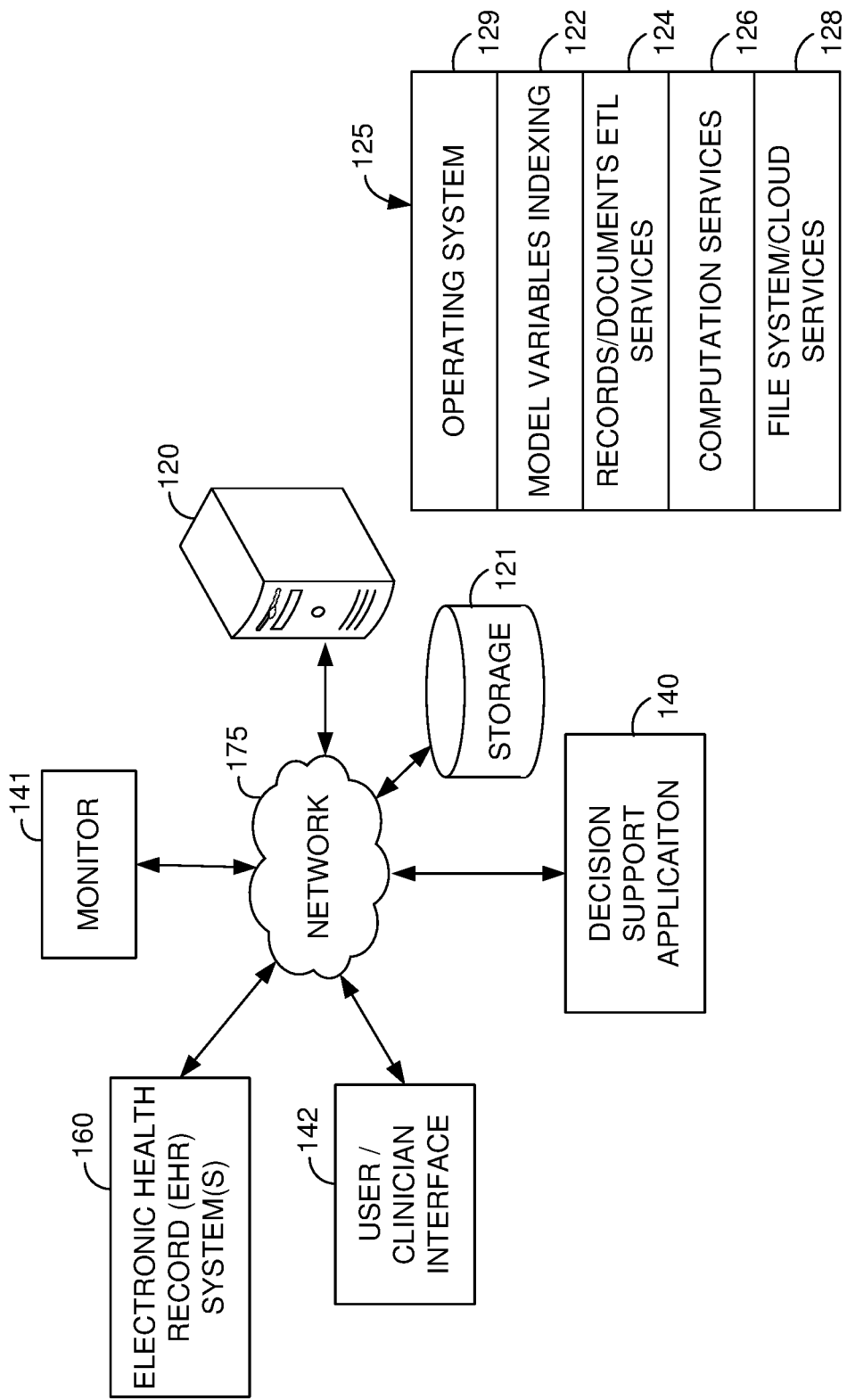
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media, as discussed further with respect to FIGS. 1A-1B.

Accordingly, at a high level, this disclosure describes, among other things, methods and systems for providing clinical decision support during usage of a ventilator using an analysis of individual breaths determining the likely presence of asynchrony between the ventilator and the patient. Patient ventilator asynchrony is a mismatch between the patient, regarding time, flow, volume or pressure demands of the patient repertory system, and the ventilator, which supplies such demands, during mechanical ventilation. In exemplary embodiments, the determination that asynchrony is likely present is generated by identifying an individual's breath within a time series of data from a ventilator providing partial ventilator support to the individual. This time series is made up of a set of measurements over a period of time from a patient's ventilator. At least some of the measurements available during the defined period of time may be used to compute the determination of the presence of asynchrony between the ventilator and the patient's breathing. The measurements used in detecting asynchrony may include volume, pressure, and flow. After detecting the breadths from the ventilator data, a plurality of features may be calculated from the ventilator data for each breadth. A set of logic is applied to the features determined for each breadth to predict the likely presence of asynchrony. In one embodiment, a set of heuristic rules are applied to the features to detect asynchrony. In another embodiment, the features for the individual breadths may be input into one or more machine learning models that are trained to predict types of asynchrony. In some embodiments, a set of heuristic rules and one or more machine learning models are utilized. For example, a set of heuristic rules may be applied to first detect the likely presence of asynchrony, and features for breadths that are flagged as indicating likely asynchrony may be input into one or more machine learning models to predict the likelihood of particular types of asynchrony being present. In a further embodiment, the identified individual breaths may be input into a set of machine learning models, which are trained to identify asynchronous features within individual breaths.

In some embodiments, the methods and systems may be implemented as a decision support computer application or tool for indicating that a patient's ventilator settings need to be adjusted. For example, asynchrony may indicate an issue present in the settings or set-up of the patient's ventilator system and may lead to respiratory distress that would will impact the health of the patient. For instance, a notification may be provided with an indication that asynchrony is present in the patient's ventilator system, and in some embodiments, a recommendation to adjust the ventilator system according to a particular type of asynchronous behavior is identified may be provided.

As previously explained, patient ventilator asynchrony is a mismatch between the neural (patient) inspiratory, regarding time, flow, volume or pressure demands of the patient respiratory system, and the mechanical inspiratory (ventilator), which supplies such demands during partial mechanical ventilation. Asynchrony between the patient and the ventilator is a common occurrence, with rates ranging from 10% to 85%. Patient ventilator asynchrony may occur due to factors related to the patient, the ventilator, or both. Alterations in respiratory drive, timing, respiratory muscle pressure, and respiratory system mechanics influence the interaction between the patient and the ventilator. Interactions between the patient and the ventilator are complicated and typically involve manual intervention by a clinician every few hours to correct patient ventilator asynchrony. The most common types of patient ventilator asynchrony are those related to triggering, such as ineffective effort, auto-triggering, and double triggering; those related to premature or delayed cycling; and those related to insufficient or excessive flow. Patient ventilator asynchrony is associated with adverse risks, including wasted work of breathing, patient discomfort, increased need for sedation, confusion during weaning from mechanical ventilation, prolonged need for mechanical ventilation, longer hospital stay, and possibly higher mortality rates. Detection and identification of asynchrony accurately, quickly and effectively leads to a quicker response to patient ventilator asynchrony and a reduction in the likely adverse impact of patient ventilator asynchrony on the individual's health.

None of the currently available partial ventilator support modes are exempt from problems with patient ventilator asynchrony. To combat the problems with patient ventilator asynchrony, it is important to accurately and promptly identify patient ventilator asynchrony so alterations to the ventilator settings may be made to correct the mismatch between the patient and the ventilator. A clinician monitoring a patient will typically only be able to monitor breadths for a short period of time that may not necessarily indicate patient ventilator asynchrony. Because accurate detection of patient ventilator asynchrony and prompt intervention often requires continuous monitoring of a patient's ventilator, there exists a need for automated patient ventilator asynchrony detection that enables quick and accurate identification of patient ventilator asynchrony.

Accordingly, embodiments of the present disclosure aim to accurately and automatically identify patient ventilator asynchrony in patients. This process may include automatically identifying patient ventilator asynchrony present in a ventilator measurement time-series for a patient being assisted by a ventilator. Specifically, embodiments include receiving patient ventilator measurements over a period of time. These measurements may include measurements of flow, pressure, and volume over a period of time. In exemplary embodiments, one or more time series may be constructed from the measurements and used with a set of rules to identify individual breaths. Applying the set of rules to determine individual breadths may involve detecting peaks within the time series. A plurality of features are determined from the ventilator data for each breath, and based on those features, embodiments of the disclosure detect the likely presence of patient ventilator asynchrony within the time interval. One or more set of heuristic rules may be utilized to identify asynchrony based on the features for each breath. Additionally or alternatively, features of one or more breaths are identified using one or more set of heuristic rules to identify one or more types of asynchrony that are occurring within the time interval.

Some embodiments of the disclosure may indicate other types of anomalies in addition to patient ventilator asynchronies. As mentioned, patient ventilator asynchrony is a mismatch of a patient's breath and mechanical ventilation and may be detected in accordance with embodiments of this disclosure using volume, pressure, and flow data. However, other anomalies may be present in that data that may similarly have a negative impact on the patient's ability to breath and health. For example, leakage is a type of anomaly that can occur when the ventilation mask is not properly positioned on the patient, resulting in ineffective ventilation. As such, some embodiments of this disclosure may detect non-asynchrony anomalies, such as leakage, using volume, pressure, and flow data. Although this disclosure utilizes examples of asynchrony, it should be understood that disclosure relating to detecting a patient ventilator asynchrony may be applied to other anomalies unless stated otherwise.

In exemplary embodiments, one or more intervening actions may be initiated based on the detection of asynchrony in the ventilator. For example, asynchrony may indicate an issue present in the settings or set-up of the patient's ventilator system and may lead to respiratory distress that would will impact the health of the patient. In this way, embodiments of this disclosure enable more accurate and timely detection of these issues causing asynchrony and lead to intervening actions to respond with proper adjustments to the ventilator system and, in some embodiments, appropriate treatment and support for a patient affected by the asynchrony. For instance, a notification may be provided with an indication that asynchrony is present in the patient's ventilator system, and in some embodiments, a recommendation to adjust the ventilator system according to a type of asynchrony that is identified may be provided. Accordingly, one aim of embodiments of this disclosure is to improve upon conventional industry practice by deriving accurate and timely detection of asynchrony and provide more effective respiratory support. In this way, current embodiments provide for a counter-conventional technological solution that is unknown in the industry and the area of clinical support.

Referring now to the drawings generally and, more specifically, referring to FIG. 1A, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural).

As shown in FIG. 1A, example operating environment 100 provides an aspect of a computerized system for compiling and/or running an embodiment of a computer-decision support tool for identifying patient ventilator asynchrony. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or more EHR systems, such as hospital EHR systems, health information exchange EHR systems, ambulatory clinic EHR systems, psychiatry/neurology EHR systems. Such EHR systems may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on storage 121, and may further include one or more computers or servers that facilitate the storing and retrieval of health records. In some embodiments, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example. Although FIG. 1A depicts an exemplary EHR system 160 that may be used for storing patient information, it is contemplated that an embodiment may also rely on decision support application 140 and/or monitor 141 for storing and retrieving patient record information, such as information acquired from monitor 141.

Example operating environment 100 further includes a provider user/clinician interface 142 communicatively coupled through network 175 to EHR system 160. Although environment 100 depicts an indirect communicative coupling between user/clinician interface 142 and EHR system 160 through network 175, it is contemplated that an embodiment of user/clinician interface 142 is communicatively coupled to EHR system 160 directly. An embodiment of user/clinician interface 142 takes the form of a graphical user interface operated by a software application or set of applications (e.g., decision support application 140) on a computing device. In an embodiment, the application includes the PowerChart® software manufactured by Cerner Corporation. In an embodiment, the application is a Web-based application or applet. A healthcare provider application may facilitate accessing and receiving information from a user or healthcare provider about a specific patient or set of patients for which the patient ventilator asynchrony is identified according to the embodiments presented herein. Embodiments of user/clinician interface 142 also facilitate accessing and receiving information from a user or healthcare provider about a specific patient or population of patients including patient history; healthcare resource data; physiological variables (e.g., vital signs) measurements, time series, and predictions (including plotting or displaying the determined outcome and/or issuing an alert) described herein; or other health-related information, and facilitates the display of results, recommendations, or orders, for example. In an embodiment, user/clinician interface 142 also facilitates receiving orders, such as orders for more resources, from a user based on the results of predictions. User/clinician interface 142 may also be used for providing diagnostic services or evaluation of the performance of various embodiments.

An embodiment of decision support application 140 comprises a software application or set of applications (which may include programs, routines, functions, or computer-performed services) residing on a client computing device, on one or more servers in the cloud, or distributed in the cloud and on a client computing device such as a personal computer, laptop, smartphone, tablet, mobile computing device, front-end terminals in communication with back-end computing systems or other computing device(s) such as computing system 120 described below. In an embodiment, decision support application 140 includes a Web-based application or applet (or set of applications) usable to provide or manage user services provided by an embodiment of the invention. For example, in an embodiment, decision support application 140 facilitates processing, interpreting, accessing, storing, retrieving, and communicating information acquired from monitor 141, EHR system 160, or storage 121, including predictions and condition evaluations determined by embodiments of the invention as described herein. In an embodiment, decision support application 140 sends a recommendation or notification (such as an alarm or other indication) directly to user/clinician interface 142 through network 175. In an embodiment, application 140 sends a maintenance indication to user/clinician interface 142. In some embodiments, application 140 includes or is incorporated into a computerized decision support tool, as described herein. Further, some embodiments of application 140 utilize user/clinician interface 142. For instance, in one embodiment of application 140, an interface component, such as user/clinician interface 142, may be used to facilitate access by a user (including a clinician/caregiver or patient) to functions or information on monitor 141, such as operational settings or parameters, user identification, user data stored on monitor 141, and diagnostic services or firmware updates for monitor 141, for example.

In some embodiments, application 140 and/or interface 142 facilitates accessing and receiving information from a user or health care provider about a specific patient, a set of patients, or a population according to the embodiments presented herein. Such information may include historical data; health care resource data; variables measurements, time series, and predictions (including plotting or displaying the determined outcome and/or issuing an alert) described herein; or other health-related information. Application 140 and/or interface 142 also facilitates the display of results, recommendations, or orders, for example. In an embodiment, application 140 also facilitates receiving orders, scheduling time with care providers (including follow up visits), or queries from a user, based on the results of the identified patient ventilator asynchrony, which may utilize user interface 142 in some embodiments.

Decision support application 140 may also be used for providing diagnostic services or evaluation of the performance of various embodiments. As shown in example environment 100, in one embodiment, decision support application 140, or the computer system on which it operates, is communicatively coupled to monitor 141 via network 175. In an embodiment, monitor 141 communicates directly (or via network 175) to computer system 120 and/or user/clinician interface 142. In an embodiment, monitor 141 comprises one or more sensor components operable to acquire clinical or physiological information about a patient and/or about a patient's medical support. For example, in exemplary embodiments, monitor 141 is associated with a device providing support to the patient, such as ventilation device. In this way, monitor 141 may provide measurements relating to the support provided to the patient via the device, such as flow, volume, and pressure of ventilator support. Additionally, the same monitor 141 or another monitor may acquire other types of clinical or physiological information about the patient, such as various types of physiological measurements, physiological variables, or similar clinical information associated with a particular physical or mental state of the patient. Such clinical or physiological information may be acquired by monitor 141 periodically, continuously, as needed, or as they become available, and may be represented as one or more time series of measured variables. It is also contemplated that the clinical or physiological information about a patient or population of patients, such as the monitored variables, patient demographics, patient history, and/or clinical narratives regarding the patient, used according to the embodiment of the invention disclosed herein may be received from a patient's historical data in EHR system 160, or from human measurements, human observations, or automatically determined by sensors in proximity to the patient.

An embodiment of monitor 141 stores user-derived data locally or communicates data over network 175 to be stored remotely. In an embodiment, decision support application 140, or the computer system it is operating on, is wirelessly communicatively coupled to monitor 141. Application 140 may also be embodied as a software application or app operating on a user's mobile device, as described above. In an embodiment, application 140 and monitor 141 are functional components of the same device, such as a device comprising a sensor, application, and a user interface. In an embodiment, decision support application 140 is in communication with or resides on a computing system that is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations such as one or more local clients and one or more remote servers and may be distributed across the other components of example operating environment 100. For example, a portion of computer system 120 may be embodied on monitor 141 or the computer system supporting application 140 for performing signal conditioning of a measured patient variable. In one embodiment, computer system 120 comprises one or more computing devices, such as a server, desktop computer, laptop, or tablet, cloud-computing device or distributed computing architecture, a portable computing device such as a laptop, tablet, ultra-mobile PC, or a mobile phone.

Embodiments of computer system 120 include computer software stack 125, which, in some embodiments, operates in the cloud as a distributed system on a virtualization layer within computer system 120, and includes operating system 129. Operating system 129 may be implemented as a platform in the cloud and is capable of hosting a number of services such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running interface 142 and/or decision support application 140. In some embodiments, user/clinician interface 142 and/or decision support application 140 operate in conjunction with software stack 125.

In embodiments, model variables indexing service 122 provide services that facilitate retrieving frequent itemsets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, model variables indexing service 122 may invoke computation services 126. Predictive models service 124 is generally responsible for providing one or more models for identifying patient ventilator asynchrony as described in connection to methods 200 and 500 of FIGS. 2 and 5, respectively.

Computation services 126 perform statistical software operations, such as computing the transformed variable predictions, transferred features (such as log and log 1p functions of features), and severity indices as described herein. In an embodiment, computation services 126 and predictive models service 124 include computer software services or computer program routines. Computation services 126 also may include natural language processing services (not shown) such as Discern nCode™ developed by Cerner Corporation, or similar services. In an embodiment, computation services 126 include the services or routines that may be embodied as one or more software agents or computer software routines. Computation services 126 also may include services or routines for utilizing performing sequential modeling using one or more models, including decision trees and logistic models, for identifying patient ventilator asynchrony, such as the models described in connection to FIGS. 2-6.

In some embodiments, stack 125 includes file system or cloud-services 128. Some embodiments of file system/cloud-services 128 may comprise an Apache Hadoop and Hbase framework or similar frameworks operable for providing a distributed file system and which, in some embodiments, provide access to cloud-based services such as those provided by Cerner Healthe Intent®. Additionally, some embodiments of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or storage 121), which, in some embodiments, includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and itemsets index information; association rulebases; agent libraries, solvers and solver libraries, and other similar information including data and computer-usable instructions; patient-derived data; and healthcare provider information, for example. It is contemplated that the term "data" used herein includes any information that can be stored in a computer storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

Figure 1B:
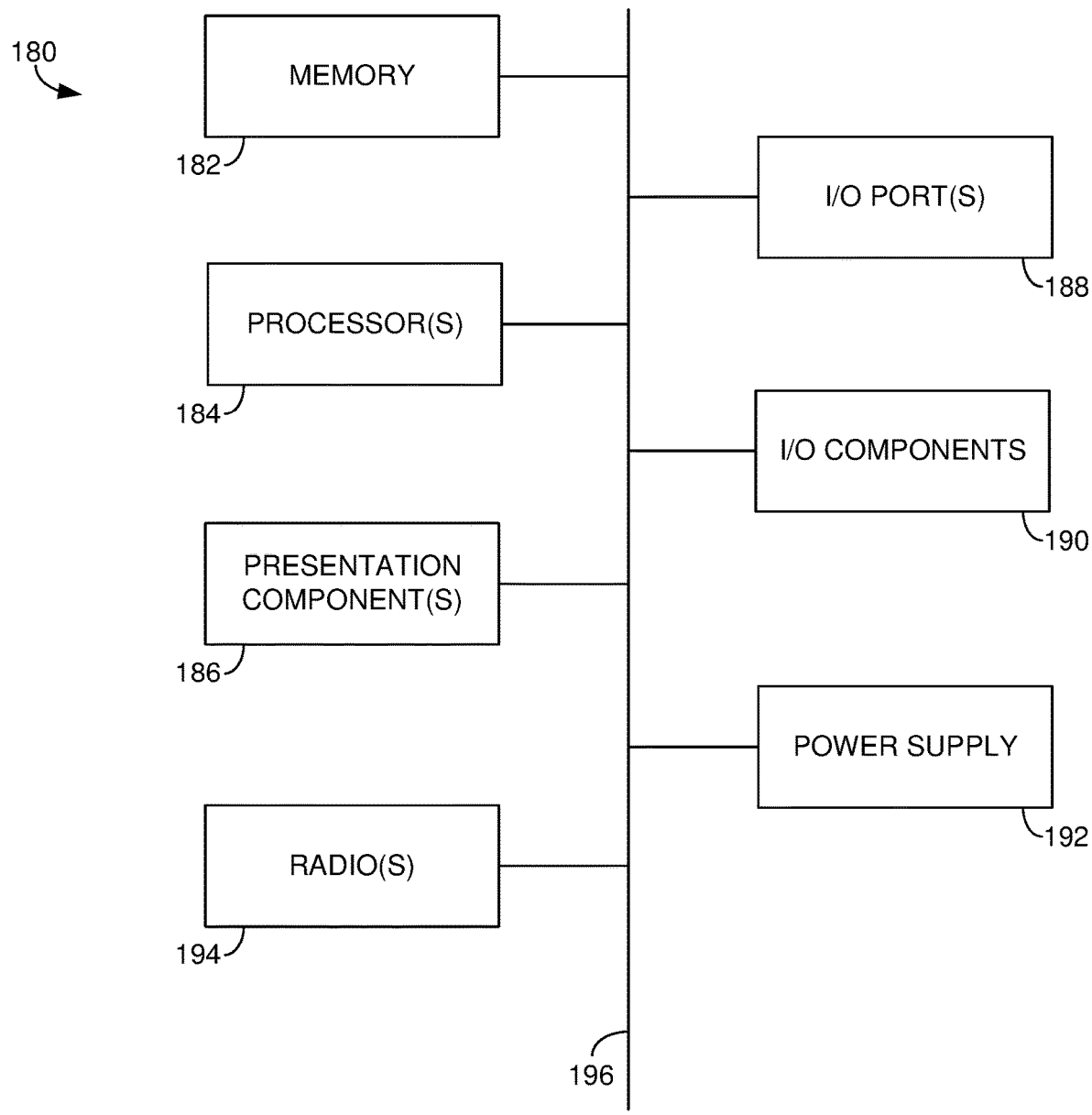

Turning briefly to FIG. 1B, there is shown one example embodiment of computing system 180 representative of a system architecture that is suitable for computer systems such as computer system 120. Computing system 180 includes a bus 196 that directly or indirectly couples the following devices: memory 182, one or more processors 184, one or more presentation components 186, input/output (I/O) ports 188, input/output components 190, radio 194, and an illustrative power supply 192. Bus 196 represents what may be one or more busses (such as an address bus, data bus, or combination thereof). Although the various blocks of FIG. 1A are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1A is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1A and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 182 includes computer storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 182 or I/O components 190. Presentation component(s) 186 present data indications to a user or other device. Exemplary presentation components include a display device, speaker, printing component, vibrating component, etc.

In some embodiments, computing system 180 comprises radio(s) 194 that facilitates communication with a wireless-telecommunications network. Illustrative wireless telecommunications technologies include CDMA, GPRS, TDMA, GSM, and the like. Radio 194 may additionally or alternatively facilitate other types of wireless communications including Wi-Fi, WiMAX, LTE, or other VoIP communications. As can be appreciated, in various embodiments, radio 194 can be configured to support multiple technologies and/or multiple radios can be utilized to support multiple technologies.

I/O ports 188 allow computing system 180 to be logically coupled to other devices, including I/O components 190, some of which may be built in. Illustrative components include a microphone, joystick, game pad, satellite dish, scanner, printer, wireless device, etc. The I/O components 190 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Decision-Support for Detecting and Identifying Patient Ventilator Asynchrony

Figure 2:
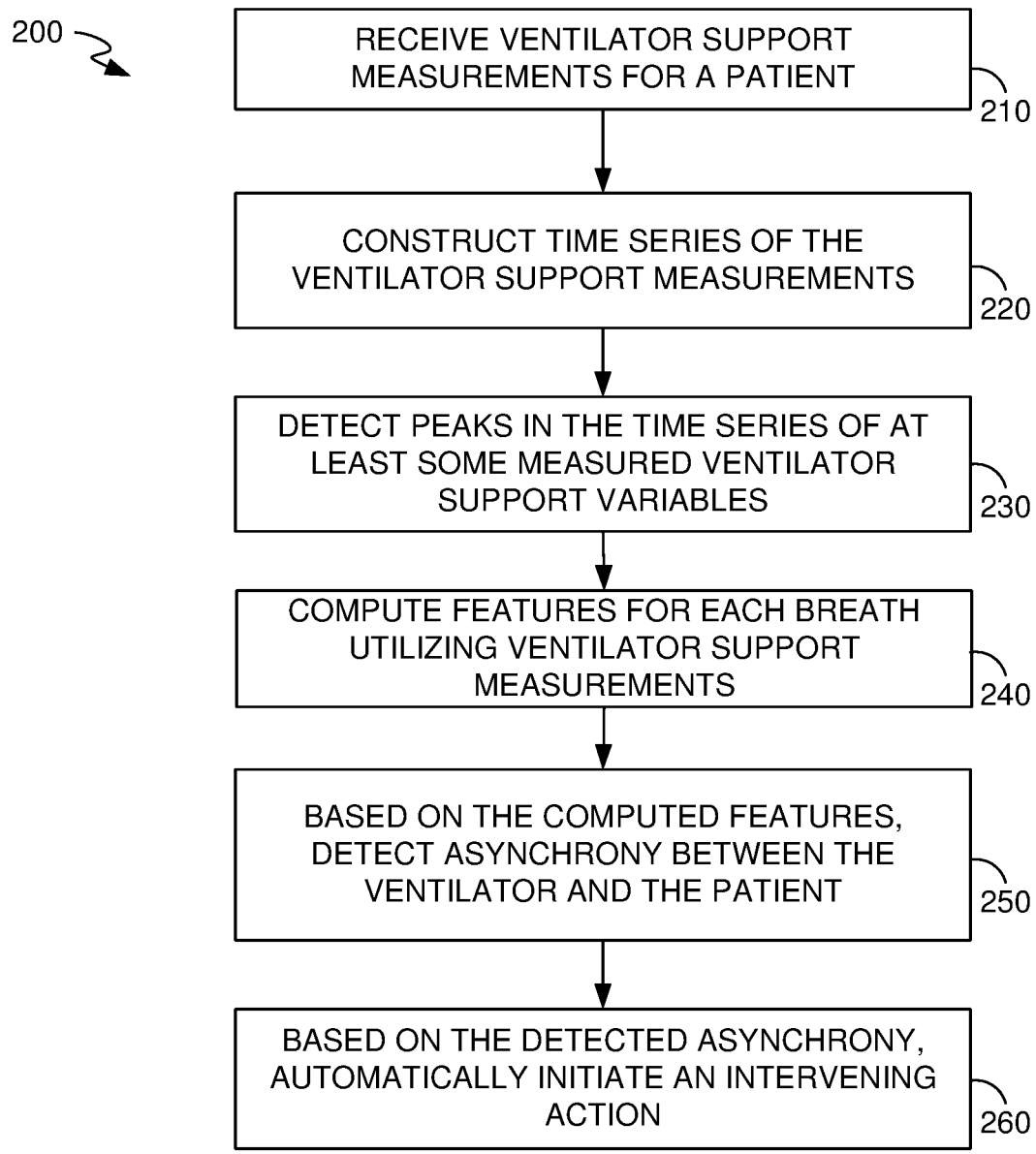
FIG. 2 depicts a flow diagram of an example method for detecting asynchrony between a patient and a ventilator in accordance with an embodiment of the disclosure.

Turning now to FIG. 2, an example embodiment of a method for detecting instances of asynchrony between the ventilator and the patient is provided and is referred to generally as method 200. In particular, example method 200 utilizes heuristic rules along with patient ventilator data available to detect a plurality of individual breaths within a time series and compute features for each breath such that potential asynchrony can be predicted within the time series. In some embodiments, method 200 is suitable for implementation as a computer-performed decision support tool or application for providing ventilatory care to patients based on detected asynchrony within a patient's time series that is more efficient than conventional technology would otherwise allow.

First, at step 210, a plurality of measurements of ventilator support variables for a patient is received. The plurality of measurements may have been acquired for the patient over a period of time while the patient is receiving partial ventilator support. In exemplary aspects, the variables include flow, volume or pressure of the provided to the patient by the ventilator. The flow, volume and pressure variables may be recorded using sensors associated with the mechanical ventilator.

The measurements for the ventilator support variables may be received from the patient's EHR, such as a medical EHR within EHR system 160 in FIG. 1, or other data storage, or may be received directly from a mechanical ventilator device, such as monitor 141. In some aspects, the variables are being monitored independently of the patient ventilator asynchrony detection system. In other words, rather than require additional monitoring to perform method 200, method 200 may leverage data that is often already being recorded in the normal course of monitoring a patient receiving partial ventilatory support. Embodiments of step 210 may acquire the physiological variable measurements continuously, periodically, or at non-regular intervals. In some embodiments, the date/time information for each measurement is stored with the measured variable values.

Next, as step 220, a time series is constructed for one or more of the ventilator support variables measured. The time series may be constructed by appending the most recent ventilator support variable measurements to the historical measurements, using the associated date/time information. In some embodiments, the historical measurements comprise measurements obtained within a recent timeframe such as the previous 20 minutes, hour, or several hours. In such embodiments, only historical measurements from within this recent timeframe are retrieved and used for the constructing time series.

In some aspects in which data is received for multiple ventilator support variables for a single patient, constructing a time series includes selecting one or more of the ventilator support variables from which data is used to identify patient ventilator asynchrony. In some aspects, for each time stamp, each of a volume data feed, a flow data feed, and a pressure data feed produce a sequence of three readings that are compiled.

In some aspects, the raw data from the ventilator support variable measurements includes one or more artifacts or some degree of electronic or other type of noise within the data. To normalize the data, portions of the noise and artifacts present in the raw data are mathematically removed by applying a smoothing algorithm to the raw data in one or more of the ventilator time series strips. An exemplary smoothing algorithm applied to the raw data is kernel density estimator. Kernel density estimation is a data smoothing solution in which inferences about the total data are made based on a finite data sample. In exemplary embodiments, boxcar and Gaussian windows are used with kernel density estimation, but it is contemplated that other windows may be used. Other exemplary smoothing algorithms that may be utilized include locally weighted polynomial regression, additive smoothing, exponential smoothing, kalman filter, Kolmogorov-zurbenko filter, laplacian smoothing, or moving average. Additionally, the ventilator time strips may be normalized at a baseline such that a minimum represents a point where the mechanical ventilator is at a minimum of activity. For example, when a pressure measurement is at zero, the ventilator is not providing any pressure to the patient at that point in time. Further, when a flow measurement is at zero, the ventilator is not providing any air flow to the patient.

Returning to method 200 of FIG. 2, at step 230, a patient's breaths are detected within time series for one or more of the measured variables. Breaths are typically indicated by peaks within pressure and volume data and, as such, determining a patient's breaths may include detecting peaks in at least one of the time series. For instance, in some embodiments, peak detection at step 230 is performed for volume and pressure time series. Such peaks detected in the time series may indicate individual breaths in a patient that is receiving partial ventilator support.

Figure 3:
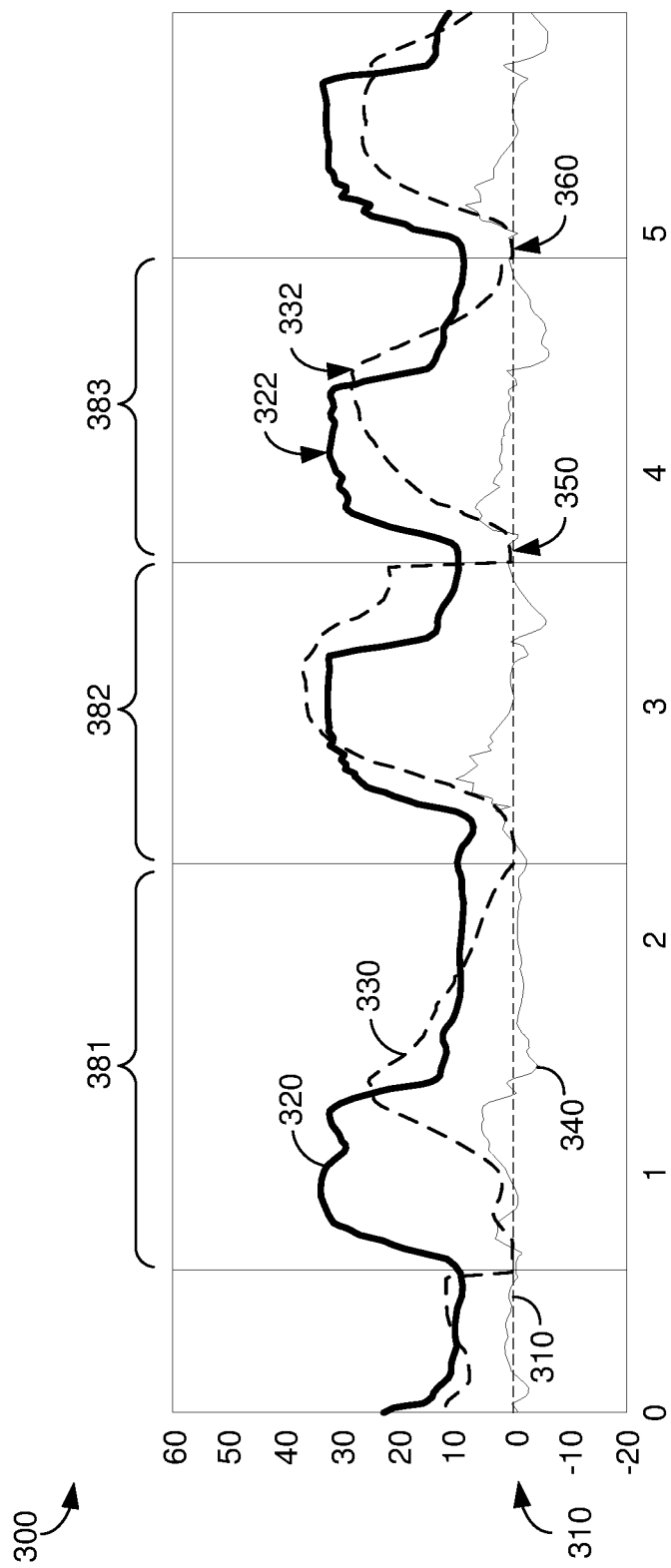
FIG. 3 depicts a graphical illustration of an exemplary time series with individual breaths identified in accordance with an embodiment of the disclosure.

Turning to FIG. 3, a strip 300 of time series for multiple ventilator variables is depicted and may be utilized to illustrate detection of a patient's individual breaths. FIG. 3, for instance, depicts time series for pressure 320, volume 330, and flow 340. In embodiments in which smoothing is performed, the strip 300 may include ventilator signal components that are a de-noised deviation from a defined baseline 310. In exemplary aspects, the baseline 310 represents a measure when the patient is not breathing or receiving mechanical ventilation. The baseline 310 may be determined from a reference population of patient or may be determined based on data specific to the patient.

In exemplary embodiments, detecting breaths involves detecting peaks within the time series. Generally, as the patient inhales for a breath, the ventilator supplies more air, resulting in an increase in pressure and volume (and, consequently, flow) from the baseline 310, and as the patient exhales, a decrease in pressure and volume (and, consequently, flow) toward the baseline 310 may be experienced. In this way, at least some peaks within the time series in strip 300 may represent breaths; however, not all peaks may represent a breath. As such, detecting breaths may include detecting peaks within one or more time series, and utilizing the detected peaks to determine breaths.

Detecting peaks may include determining the largest local maxima for one or more variables within a time interval. For example, a peak may be detected by determining the largest local maximum for pressure within the pressure time series 320 over a time interval and/or largest local maximum for volume within the volume time series 330 over the time interval. A local maximum may comprise the greatest increase in the variable, such as pressure or volume, from the baseline within the time period. FIG. 3 identifies local maximum 322 for pressure and local maximum 332 for volume.

In some embodiments, identifying a peak may also include identifying local minimum values for the variables. A local minimum may be determined as a greatest deviation from the baseline in the negative direction within the time interval and, if there is no deviation in the negative direction, the smallest deviation from the baseline in the positive direction.

A peak may begin at a point where the measurements for the variable, such as volume or pressure, begin to increase and may end when the variable measurements reaches the next lowest point before beginning to increase again. In other words, a peak may be between two successive minimums, where the peak identified represents an inflection point where the ventilator begins to decrease the amount of air pressure and volume provide to the patient. For example, peak representing local maximum 332 in volume time series 330 is between minimums 350 and 360. From the identified peak maxima, individual breaths can be identified by a breath beginning at one peak maxima and ending at a subsequent peak maxima. In exemplary embodiments, peaks are detected in pressure and volume time series. In other embodiments, peaks may also be detected in time series for other variables, such as flow. Further, example aspects of a computer routine covering implementations of peak detection are illustratively depicted in FIG. 7A.

Identification of an individual breath may be accomplished by determining whether a detected peak (i.e., a local maximum) satisfies a threshold deviation from baseline 310. For example, in exemplary aspects, the local maximum of a peak satisfies a predetermined threshold peak deviation (which may also be referred to as a threshold maximum peak height) if it is greater than the predetermined threshold peak deviation. Peaks that do not satisfy the threshold peak deviation may not be considered to represent actual breaths. In some embodiments, the threshold peak deviation is a predetermined variation that is the same for all peaks. In other embodiments, the threshold peak deviation is based on the width of the peak (i.e., time between two successive local minimums between which the peak is detected). For example, a threshold peak deviation may be 80% to 90% of the peak width.

Additionally, in exemplary aspects, to determine whether a peak represents an actual breath rather than noise or an artifact, it may be determined whether the variables values within the peak satisfy a predetermined threshold deviation for a minimum period of time. The predetermined threshold deviation may be the same as or less than the threshold peak deviation. Further, in some embodiments, detecting a breath from a peak includes determining that the peak width, or time between successive minimums, satisfies a predetermined threshold peak width. The threshold peak width may be satisfied when the peak width is greater than or equal to the threshold peak width. The strip 300 of FIG. 3 depicts three complete breaths (breaths 381, 382, and 383) detected in accordance with an embodiment of this disclosure. Further, example aspects of a computer routine covering implementations of breath detection from detected peaks are illustratively depicted in FIG. 7B.

Returning to method 200 of FIG. 2, detection of a patient's breath at step 230 of method 200 may be performed as described with respect to FIG. 3. As explained above, exemplary embodiments of this disclosure identify peaks (and, thus, breaths) by identifying maximum and, in some instances minimum, values of pressure and volume. However, in other aspects, peaks and breaths may be detected also utilizing flow values in a similar manner.

At step 240 of method 200, features are computed for each breath within individual breaths. These features are calculated from variable measurements, such as pressure, volume, and flow measurements, for the identified individual breaths. For example, step 240 may include computing a plurality of pressure features based on pressure measurements within a time period corresponding to a detected breath and computing these pressure features for a plurality of breaths. Additionally, one or more of the computed pressure features may be based on pressure values spanning across multiple breaths. In one embodiment, the following features are calculated relating to pressure:

Pressure range may be calculated by subtracting the minimum pressure from the maximum pressure within an individual breath.

Pressure peaks may be calculated by calculating the number of pressure peaks within an individual breath.

Pressure peak time is the time between the first pressure peak and the last pressure peak if there are multiple peaks in an individual breath.

Pressure peak difference calculates the pressure difference between the highest and lowest peak if there are multiple pressure peaks within an individual breath.

Pressure peak start may be calculated from the time after a breath begins to when the first pressure peak occurs with an individual breath.

Pressure peak oscillation may be calculated from the distance between the highest peak and the lowest valley within an individual breath.

Pressure width may be calculated from the time where the pressure peak is at least 60% of the maximum peak pressure.

Pressure peak time to next may be calculated from the time between the first peak of one breath to the first peak of the next breath.

Pressure peak time to previous may be calculated from the time between the first peak of one breath and the first peak in the previous breath.

Pressure peak ratio may be calculated from the ratio between pressure peak time to next and the pressure peak to previous.

Pressure in integral may be calculated from the integral of pressure during inhalation.

Pressure out integral may be calculated from the integral of pressure during exhalation.

Pressure integral ratio may be calculated from a ratio of integrals during inhalation and exhalation.

Step 240 may further include computing a plurality of volume features based on volume measurements within a time period corresponding to a detected breath and computing these volume features for a plurality of breaths. Additionally, one or more of the computed volume features may be based on volume values spanning across multiple breaths. In one embodiment, the following features are calculated relating to volume:

Max volume of oscillation may be calculated from a difference of minimum and maximum volume during a time when the volume is at least 70% of the maximum volume within an individual breath.

Volume peak width may be calculated from a time during which the volume is at least 70% of the maximum volume within an individual breath.

Inhalation volume may be calculated from the inhalation volume within an individual breath.

Out volume may be calculated from the exhalation volume within an individual breath.

End volume drop may be calculated from the discontinuous drop of volume at the end of the breath within an individual breath.

In time may be calculated from the time of inhalation within an individual breath.

Out time may be calculated from the time of exhalation within an individual breath.

Time ratio may be calculated from a ratio of in time and out time within an individual breath.

Volume oscillation ratio may be calculated from a ratio of the max volume oscillation and the in volume within an individual breath.

Volume peak time to next may be calculated from a distance between the current breath's peak to the next breath's peak.

Volume peak time to previous may be calculated from a distance between the current breath's peak to the previous breath's peak.

Volume peak time ratio may be calculated from a ratio between the volume peak time to next and the volume peak time to previous.

Flow ratio may be calculated from a ratio of exhalation volume and inhalation volume within an individual breath.

Step 240 may also include computing a plurality of flow features based on flow measurements within a time period corresponding to a detected breath and computing these flow features for plurality of breaths. Additionally, one or more of the computed flow features may be based on flow values spanning across multiple breaths. In one embodiment, the following features are calculated relating to flow:

Flow maximum may be calculated from the maximum flow in an individual breath.

Flow minimum may be calculated from the minimum flow in an individual breath.

Flow exhalation valleys may be calculated from the number of valleys in flow during exhalation in an individual breath.

Flow exhalation valleys time may be calculated from the time between the first valley and the last valley during exhalation in an individual breath where there are multiple valleys.

Flow exhalation valleys range may be calculated from the range of flow between the first valley and last valley during exhalation in an individual breath where there are multiple valleys.

Some embodiments of step 240 may include calculating other features, which may include features based on individual breaths or a comparison between individual breaths. In one embodiment, the following features are calculated:

Respiratory rate may be calculated a number of breaths taken over a time interval, such as breaths per minute.

Phase area flow pressure may be calculated from the area enclosed by the flow-pressure curve within an individual breath.

Phase area flow volume may be calculated from the area enclosed by the flow-volume curve within an individual breath.

Phase area volume pressure may be calculated from the area enclosed by the volume-pressure curve within an individual breath.

Once features are computed based on the detected breaths, the feature values may be utilized detect the presence of asynchrony at step 250. In some embodiments, detecting the presence of asynchrony at step 250 includes detecting the presence of patient ventilator asynchrony and/or other types of anomalies with the mechanical ventilation system, such as leakage.

Figure 4:
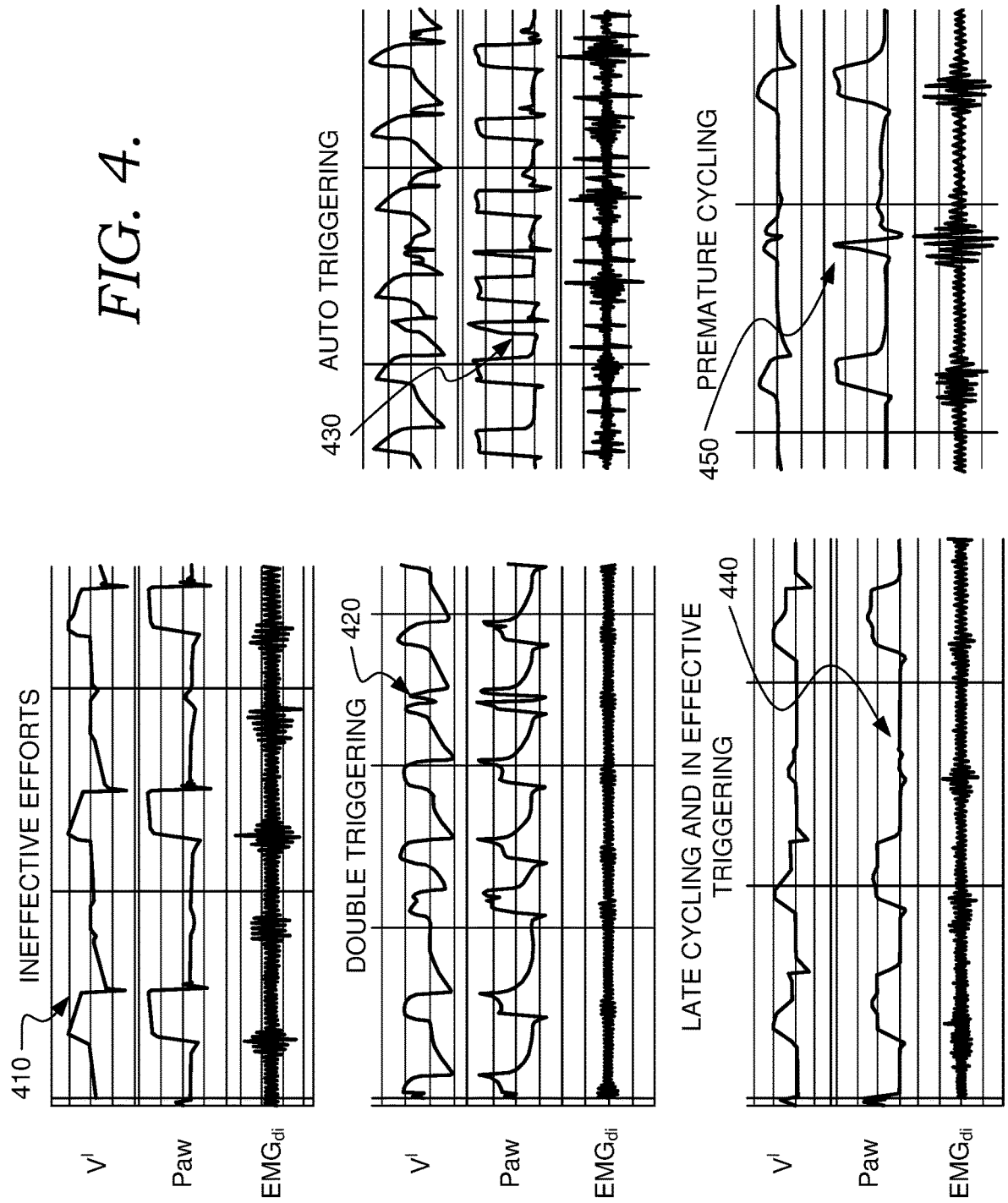
FIG. 4 depicts graphical illustrations of an exemplary time series with types of asynchronies identified in accordance with an embodiment of the disclosure.

Several types of anomalies, including asynchronies, may occur during partial ventilatory support. These types of asynchronies may describe how a mechanical ventilator may be out of sync with a patient's respiratory needs or otherwise become ineffective. FIG. 4 provides exemplary time series strips for patients experiencing patient ventilator asynchrony with asynchrony identified. Ineffective efforts asynchrony 410 occurs when a patient is attempting to breath but the mechanical ventilator is not supplying the patient with adequate air. Double triggering asynchrony 420 occurs where the mechanical ventilator turns on and then turns back off. Auto triggering asynchrony 430 occurs where there is a spurious breath and the ventilator identified a problem and attempted to correct the issue. Late cycling and ineffective triggering asynchrony 440 occurs when a breath is skipped by the mechanical ventilator and the patient is attempting to breathe without any air supplied by the mechanical ventilator. Premature cycling asynchrony 450 occurs when the mechanical ventilator does not supply sufficient air to meet the patient's needs. Flow asynchrony occurs when the amount of air provided by the mechanical ventilator and amount of air returned by the patient should does not match. Leakage occurs when air leaks out of the side of the mask which may indicate an improper functioning of the ventilator mask and only a portion of the air supplied by the mechanical ventilator will get to the patient.

In exemplary aspects, detecting the presence of asynchrony at step 250 comprises determining the presence of a particular type of asynchrony and/or a broader group of asynchrony. Step 250 includes applying a set of logic the computed detected to detect asynchrony. In some embodiments, the logic comprises a set of heuristic rules. In some embodiments, heuristic rules are applied to the calculated features to detect the likely presence of one or more groups of asynchronies or other anomalies. The asynchronies and anomalies may be grouped together by common signs, such as inconsistent volume peak-to-peak times.

In example embodiments, step 250 includes applying heuristic rules to identify the likely presence of one or more of five groups and each group may correspond to one or more specific types of asynchronies or other anomalies. For instance, group 1 may be categorized by incomplete exhalation and may represent possible leakage behavior. An exemplary set of rules to identify this group 1 may include determining group 1 is likely present if the flow ratio is less than 0.6. Group 2 may be categorized as a high oscillation in volume near the peak and may represent possible double triggering or ineffective triggering asynchronous behavior. An exemplary set of rules to identify group 2 may include determining group 2 is likely present if the volume oscillation ratio is greater than 0.25. Group 3 may be categorized as inconsistent volume peak-to-peak times and may represent possible auto-triggering, double triggering, or ineffective triggering asynchronous behavior. An exemplary set of rules to identify group 3 may include determining group 3 is likely present if the volume peak time ratio is less than 0.7. Group 4 may be categorized as inconsistent pressure peak-to-peak times and may represent possible auto-triggering, premature cycling, and double triggering asynchronous behavior. An exemplary set of rules to identify group 4 may include determining group 4 is likely present if the pressure peak time ratio is less than 0.6. Group 5 may be characterized by low exhalation time relative to inflation time and may represent possible detect flow asynchronous behavior. An exemplary set of rules to identify group 5 may include determining group 5 is likely present if the time ratio is less than 0.8. Example aspects of a computer routine covering implementations of group detection utilizing the above heuristic rules are illustratively depicted in FIG. 7C.

In some embodiments, the logic applied at step 250 comprises one or more machine learning models. In exemplary embodiments, a generalized uniform manifold approximation and projection for dimension reduction (UMAP) model is utilized to predict a specific type of asynchrony (e.g., double triggering, premature cycling) or other type of anomalies (e.g., leakage). In this way, this embodiment of step 250 may generate a more specific prediction of an instance of asynchrony or other types of anomalies. The one or more machine learning models may be trained as described below with respect to FIG. 5.

In some embodiments, step 250 includes applying both a set of heuristic rules and one or more machine models. For examples, a set of heuristic rules may be applied to detect potential asynchrony or other anomaly using all of the available data, and computed features for breaths detected as indicating possible asynchrony or other anomaly may be input into the one or more machine learning models to detect the likely presence of a specific type of asynchrony or other anomaly. In this way, the measurement data may be narrowed using the heuristic rules before applying the one or more machine learning models.

Returning to method 200 of FIG. 2, at step 260, one or more intervening actions may be initiated based on the identified asynchrony. In some embodiments, an intervening action may include emitting or otherwise electronically communicating a recommendation or notification to a caregiver responsible for the patient's care, such as a physician or nurse. This notification may be presented via a user/clinician interface (such as interface 142 described in FIG. 1A). The notification may indicate the specific type of asynchronous behavior occurring between the patient and the mechanical ventilator or a group of anomaly that includes asynchronous behavior. A recommendation for treatment and support may be provided based on the type of asynchrony or anomaly group detected. Such a recommendation may include a recommendation to adjust one or more settings of the ventilator, such as volume, pressure, or flow, to correct the asynchrony or anomaly. Other types of recommendations may include ordering additional supervision to have a caregiver monitor the asynchronous behavior further or ordering medications and treatments to reduce the impact of the asynchrony of the patient's health. Additionally, some embodiments of step 260 may further include storing the result of the identified asynchrony in an EHR associated with the patient and further may include providing the patient's EHR (or facilitating access to the EHR) in the notification.

In example embodiments, an intervening action may include modifying the patient's ventilator settings to compensate for or correct the asynchronous behaver identified. The modified ventilator settings may include adjusting the flow, volume or pressure of the mechanical ventilator (which may require further examination by a care provider). An intervening action may also include electronically adding one or more documents with special ventilator setting adjustment instructions to a queue associated with the patient's record. One or more care providers, such as a clinician in charge of the patient's care, may be notified of the setting modification.

One or more of these intervening actions may be performed by automatically modifying computer code executed in a healthcare software program for adjusting mechanical ventilator settings, thereby transforming the program at runtime. For example in one embodiment, the modification comprises modifying (or generating new) computer instructions to be executed at runtime in the program, the modification may correspond to a change in a ventilator setting due to the identified patient ventilator asynchrony.

Figure 6:
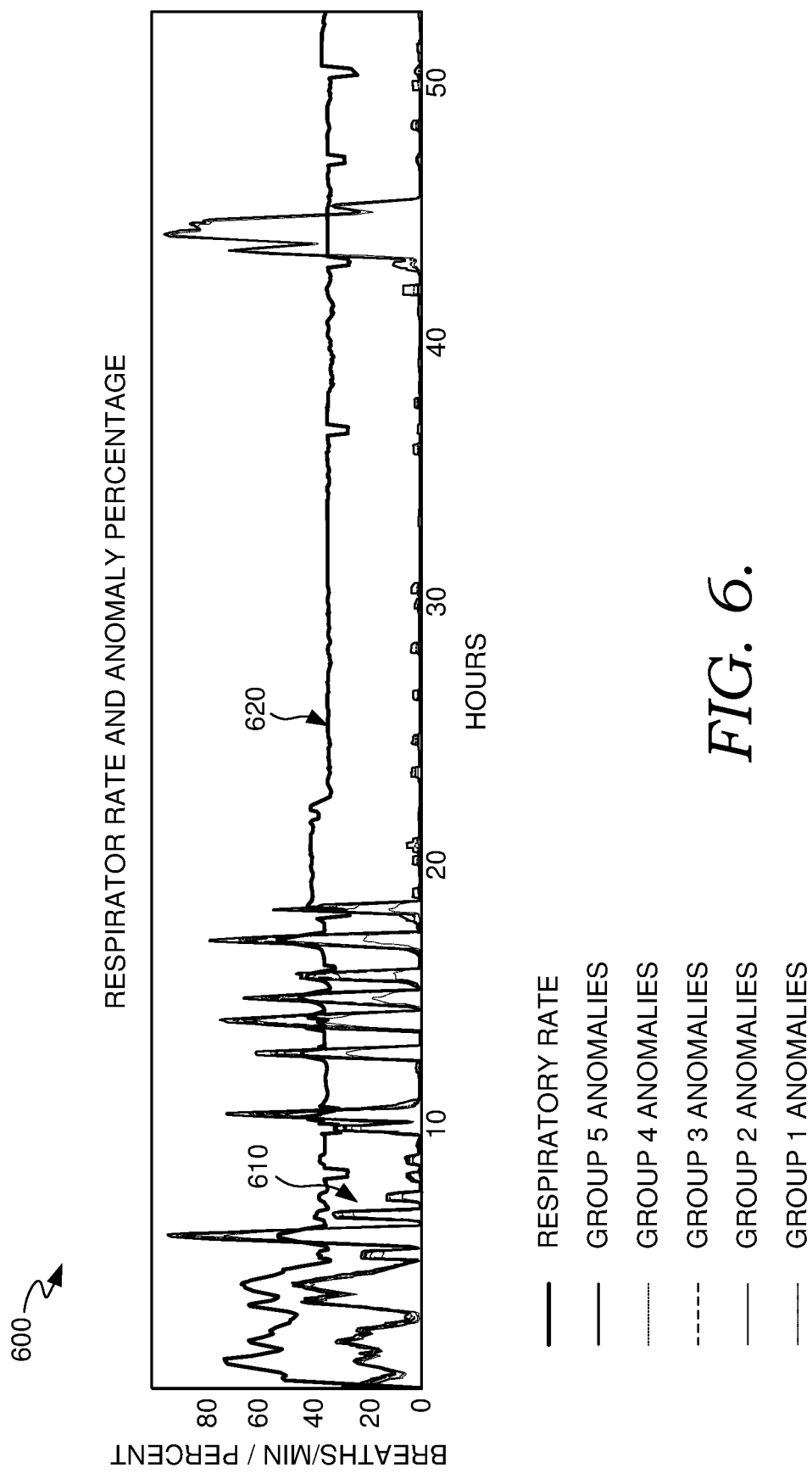
FIG. 6 depicts an example graphical user interface that may be generated in response to detect asynchrony in accordance with an embodiment of the disclosure.

FIG. 6 depicts an example graphical user interface component that may be generated and presented on a user interface, such as interface 142 in FIG. 1A, in response to detecting asynchrony in accordance with an embodiment of the disclosure. The graphical user interface of FIG. 6 provides an exemplary asynchrony time series 600, indicating detected asynchronies for a patient over time. The asynchronies may be detected in accordance with an embodiment of method 200 in FIG. 2.

The first portion 610 of the time series 600 in the graphical user interface indicate the percent of the patient's breaths within a time window that an asynchrony or other type of anomaly was detected. In this example, groups of anomalies are detected, and the first portion indicates the percentage of breaths that the group was detected. As illustrated, multiple types of anomalies, including asynchronies, may be detected within the same time window, with group 1 anomalies being the most prevalent detected for this patient. In some embodiments, the different symbols or colors are used for each group of detected anomalies so that a user can quickly assess the relative amounts of the different types of anomalies based on the relative amounts of symbols or colors present.

The time series 600 includes a second portion 620 that identifies the patient's respiratory rate over the same time period as the detected anomalies. In this example, the second portion 620 overlays the first portion 610 so that a view can easily identify a relationship between respiratory rate and the detected anomaly groups as the asynchronies and other anomalies will have an impact on the patient's breathing. FIG. 6 depicts how the patient's respiratory rate is higher during times of more continuous presence of asynchronies and other anomalies, such as between 0 hours and approximately 6 hours.

Building a Patient Ventilator Asynchrony Identifier

Figure 5:
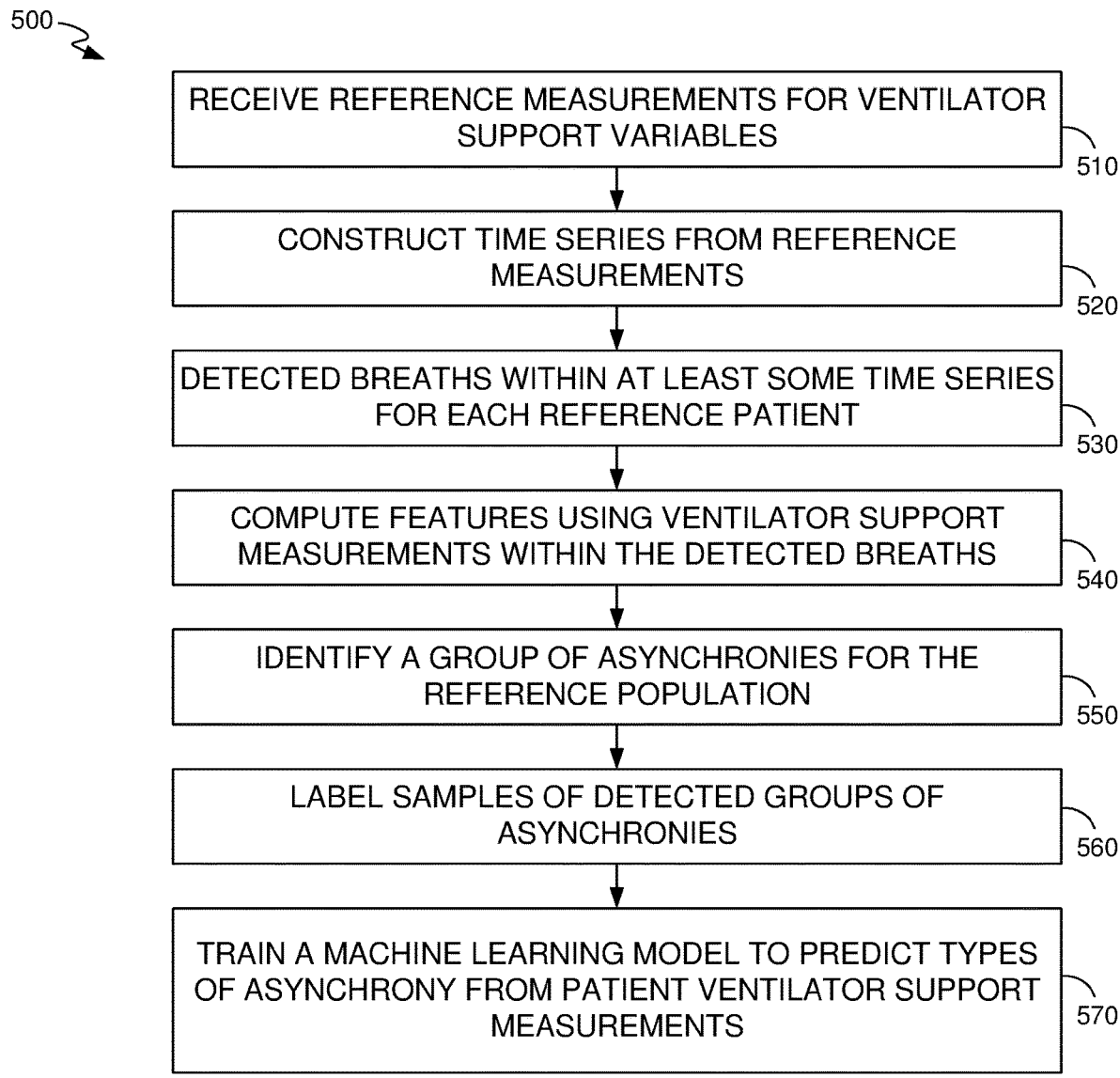
FIG. 5 depicts a flow diagram of an example method for building a patient ventilator asynchrony identifier in accordance with an embodiment of the disclosure.

FIG. 5 illustrates an example process 500 for building a patient ventilator asynchrony identifier, including selecting features for use in the predictor, are provided. As described in greater detail below with respect to FIG. 5, a variety of machine learning models may be utilized in identifying patient ventilator asynchrony. For instance, identification model(s) may be used to identify patient ventilator asynchrony. Additionally, these models may use different types of machine learning algorithms. For instance, a first type (such as a gradient boosted tree model) may be used to select features for a potential feature pool, a second type (such as an adaptive GLMnet) may be used for selecting final feature sets, and a third type (such as generalized linear models) such as may be used for generating the actual prediction.

At step 510, a plurality of measurements for a set of reference patients who have received partial ventilator support is received. The reference population of patients includes patients who have received partial ventilator support. The patient data may include flow, volume and pressure measurements over time received when using mechanical ventilation.

At step 520, the reference patient data may be used to construct individual time series for each patient in the reference patient data set. For embodiments in which flow, volume, and pressure measurements are received, step 520 may include constructing time series for flow, volume, and/or pressure for each reference patient. Embodiments of step 520 may be similar to step 220 in FIG. 2.

At step 530, breaths are detected from the time series for each reference patient. Breath detection may be performed in accordance with embodiments of step 230 in FIG. 2. At step 540, a plurality of features, such as volume-based features, pressure-based feature, and flow-based features, are calculated using measurements within the detected breaths. The features may be computed in accordance with an embodiment of step 240 in FIG. 2.

At step 550, the above calculated features may be used to identify one or more group of asynchronies or other anomalies for the reference population where each group may represent one or more specific types of asynchronies or other anomalies. These groups may be detected from the calculated features using a set of heuristic rules as described above with respect to some embodiment of step 250 of FIG. 2.

At step 560, samples from the above identified groups of asynchronies and other anomalies labeled by one or more experts. The experts may include a group of domain experts with experience reading ventilator strips. Experts may label each individual breath within the samples using a number of categories to train a machine learning model. The categories for labeling the individual breaths may include but are not limited to:

Normal
Cough
Suction
Flow asynchrony
Ineffective efforts
Auto triggering
Premature cycling
Double triggering
Late cycling
Data collection glitch
Leakage
Other At step 570, one or more machine learning models are trained using the hand-labeled samples from step 260 as ground truth data along with least some features computed for the reference population. In exemplary aspects, the machine learning model is a generalized uniform manifold approximation and projection for dimension reduction (UMAP). For instance, the model may be used to reduce dimensionality of the provided data in a semi-supervised system that provides at least a portion of known clusters such that the UMAP model can reduce the dimensionality and predict future results. Using a semi-supervised model can use all of the engineered features to leverage expert knowledge in combination with machine learning. It is contemplated that other types of machine learning models may be utilized, such as generalized linear models. In other embodiments, the one or more machine learning models include a neural network or gradient boosting.

Many different arrangements of the various components depicted, as well as components not shown, are possible without departing from the spirit and scope of the present invention. It will be understood that certain features and sub-combinations are of utility and may be employed without reference to other features and sub-combinations and are contemplated within the scope of the claims. Not all steps listed in the various figures need be carried out in the specific order described. Accordingly, the scope of the invention is intended to be limited only by the following claims.

What is claimed is:

1. One or more non-transitory computer storage media having computer-executable instructions embodied thereon that, when executed on a computerized decision support system using one or more hardware processors, cause the one or more hardware processors to facilitate performance of a plurality of operations associated with a healthcare software program, the operations comprising:

receiving a plurality of measurements taken by a ventilator associated with a patient, the plurality of measurements being acquired over a time span;

constructing one or more time series from the plurality of measurements for the ventilator to detect:
(a) a plurality of peak measurement values using at least one of the one or more time series; and
(b) a plurality of breaths of the patient corresponding to the plurality of peak measurement values;
for each breath of the plurality of breaths, computing a plurality of features based on the plurality of measurements, the plurality of features selected from a group comprising at least:
a flow ratio calculated from a ratio of exhalation volume and inhalation volume within an individual breath;
a volume oscillation ratio calculated from a ratio of a maximum volume oscillation and an in volume within an individual breath, wherein the maximum volume oscillation is calculated from a difference of minimum and maximum volume during a time when a volume is at least 70% of a maximum volume within an individual breath;
a volume peak time ratio calculated from a ratio between a volume peak time to next and a volume peak time to previous, wherein the volume peak time to next is calculated from a distance between a current breath's peak to the next breath's peak and the volume peak time to previous is calculated from a distance between the current breath's peak to a previous breath's peak;
a pressure peak time ratio calculated from a ratio between a pressure peak time to next and a pressure peak time to previous, wherein the pressure peak time to next is calculated from the time between a first peak of one breath to a first peak of a next breath and the pressure peak time to previous is calculated from the time between the first peak of one breath and a first peak in a previous breath; and
a time ratio calculated from a ratio of in time and out time within an individual breath;
detecting one or more asynchronies between the patient and the ventilator responsive to determining that the plurality of features correspond to one or more phenomena from a group comprising at least:
a flow ratio less than 0.6;
a volume oscillation ratio greater than 0.25;
a volume peak time ratio less than 0.7;
a pressure peak time ratio less than 0.6; and
a time ratio less than 0.8; and
responsive to detecting the one or more asynchronies:
automatically initiating an intervening action, wherein:
the intervening action comprises adjusting via the one or more hardware processors at least one of flow, volume, or pressure of the ventilator, and
the intervening action facilitates at least one effect from a group comprising:
reducing a detected presence of the one or more asynchronies;
reducing an adverse effect associated with the one or more asynchronies;
countering the detected presence of the one or more asynchronies; and
countering the adverse effect associated with the one or more asynchronies.

2. The one or more non-transitory computer storage media of claim 1, wherein: the plurality of measurements comprise volume, pressure, and flow measurements; the one or more asynchronies comprise double triggering, auto triggering, premature cycling, or flow asynchrony; and the operations further comprise detecting one or more peaks within a series selected from a group comprising a volume time series, a pressure time series, and a flow time series.

3. The one or more non-transitory computer storage media of claim 1, wherein detecting the one or more asynchronies comprises applying a set of heuristic rules to the plurality of features for each breath to determine one or more anomaly groups that represent at least one asynchrony.

4. The one or more non-transitory computer storage media of claim 3, wherein detecting the one or more asynchronies further comprises applying one or more machine-learning electronic models to detect a likelihood of the one or more asynchronies being present.

5. The one or more non-transitory computer storage media of claim 4, wherein the set of heuristic rules is applied to a plurality of features before the one or more machine-learning electronic models are applied.

6. The one or more non-transitory computer storage media of claim 1, wherein constructing the one or more time series includes applying a smoothing algorithm, and wherein automatically initiating the intervening action comprises one or more operations selected from a group comprising electronically communicating a notification to a caregiver assigned to the patient, providing a recommendation to modify settings on the ventilator, and initiating an order for additional care for the patient.

7. The one or more non-transitory computer storage media of claim 1, wherein the operations further comprise after automatically initiating the intervening action:
computing features associated with a subsequent breath based on additional measurements taken by the ventilator subsequent to the plurality of measurements;
detecting an asynchrony associated with the subsequent breath based on the features associated with the subsequent breath; and
initiating a second intervening action based on the asynchrony associated with the subsequent breath.

8. The one or more non-transitory computer storage media of claim 7, wherein the intervening action and the second intervening action comprise a first ventilator adjustment performed in response to the automatic initiating and a second ventilator adjustment performed after the first ventilator adjustment, respectively.

9. The one or more non-transitory computer storage media of claim 1, wherein detecting the one or more asynchronies is based on a machine-learning electronic model, and wherein:
(a) the machine-learning electronic model is trained by inputting, to the machine-learning electronic model, vectors of data corresponding to instances of information associated with one or both of the plurality of features and the plurality of breaths, wherein the training of the machine-learning electronic model is based on learning weights associated with the instances of information, and
(b) detecting the one or more asynchronies comprises applying, to the trained machine-learning electronic model, information associated with data selected from a group comprising the plurality of features and the plurality of the breaths to facilitate the detection of the one or more asynchronies.

10. The one or more non-transitory computer storage media of claim 1, wherein the operations further comprise:
automatically adjusting a ventilator setting in response to detecting the one or more asynchronies.

11. The one or more non-transitory computer storage media of claim 10, wherein the operations further comprise:
after automatically adjusting the ventilator setting, (a) constructing one or more additional time series from additional measurements taken by the ventilator corresponding to a subsequent time span and (b) based on additional features computed from the additional measurements, detecting one or more additional asynchronies between the patient and the ventilator; and
automatically adjusting at least one of a group of ventilator settings based on the one or more additional asynchronies.

12. The one or more non-transitory computer storage media of claim 11, wherein the operations further comprise detecting an individual breath of the patient in response to identifying one or more peak measurement values in the one or more additional time series, and wherein the additional features are computed for the individual breath from the additional measurements.

13. The one or more non-transitory computer storage media of claim 1, wherein the operations further comprise:
labeling one or more groups of anomalies, detected within each of the one or more time series, based on the plurality of features for each breath, wherein the one or more groups of anomalies comprise a type of asynchrony;
training a machine-learning electronic model, based on training data corresponding to the labeled groups of anomalies and the plurality of features; and
applying the machine-learning electronic model to information associated with the plurality of measurements to identify instances of asynchrony between the patient and the ventilator.

14. The one or more non-transitory computer storage media of claim 1, wherein the operations further comprise:
training a machine-learning electronic model using training data corresponding to information associated with (a) instances of measurement data relating to ventilator and patient respiratory operations and (b) matches, mismatches, or asynchronies indicated by the instances of measurement data, wherein the training comprises performing a data transformation configured to reduce a dimensionality of the training data; and
inputting to the trained machine-learning electronic model one or more input sets of information to predict one or more asynchronies between the patient and the ventilator, wherein the one or more input sets of information are associated with the plurality of measurements and the plurality of features for each breath.

15. The one or more non-transitory computer storage media of claim 14, wherein the training comprises performing a data transformation configured to reduce a dimensionality of the training data.

16. The one or more non-transitory computer storage media of claim 1, wherein detecting one or more asynchronies comprises performing a data transformation configured to reduce a dimensionality of data associated with the plurality of measurements.

17. A computerized decision support system having one or more hardware processors configured to facilitate performance of a plurality of operations associated with a healthcare software application, the operations comprising:
receiving a plurality of measurements taken by a ventilator associated with a patient, the plurality of measurements being acquired over a time span;
constructing one or more time series from the plurality of measurements for the ventilator to detect:
(a) a plurality of peak measurement values using at least one of the one or more time series; and
(b) a plurality of breaths of the patient corresponding to the plurality of peak measurement values;
for each breath of the plurality of breaths, computing a plurality of features based on the plurality of measurements, the plurality of features selected from a group comprising at least:
a flow ratio calculated from a ratio of exhalation volume and inhalation volume within an individual breath;
a volume oscillation ratio calculated from a ratio of a maximum volume oscillation and an in volume within an individual breath, wherein the maximum volume oscillation is calculated from a difference of minimum and maximum volume during a time when a volume is at least 70% of a maximum volume within an individual breath;
a volume peak time ratio calculated from a ratio between a volume peak time to next and a volume peak time to previous, wherein the volume peak time to next is calculated from a distance between a current breath's peak to the next breath's peak and the volume peak time to previous is calculated from a distance between the current breath's peak to a previous breath's peak;
a pressure peak time ratio calculated from a ratio between a pressure peak time to next and a pressure peak time to previous, wherein the pressure peak time to next is calculated from the time between a first peak of one breath to a first peak of a next breath and the pressure peak time to previous is calculated from the time between the first peak of one breath and a first peak in a previous breath; and
a time ratio calculated from a ratio of in time and out time within an individual breath;
detecting one or more asynchronies between the patient and the ventilator responsive to determining that the plurality of features correspond to one or more phenomena from a group comprising at least:
a flow ratio less than 0.6;
a volume oscillation ratio greater than 0.25;
a volume peak time ratio less than 0.7;
a pressure peak time ratio less than 0.6; and
a time ratio less than 0.8; and
responsive to detecting the one or more asynchronies:
automatically initiating an intervening action,
wherein:
the intervening action comprises adjusting via the one or more hardware processors at least one of flow, volume, or pressure of the ventilator, and
the intervening action facilitates at least one effect from a group comprising:
reducing a detected presence of the one or more asynchronies;
reducing an adverse effect associated with the one or more asynchronies;
countering the detected presence of the one or more asynchronies; and
countering the adverse effect associated with the one or more asynchronies.

18. The computerized decision support system of claim 17, wherein the asynchronies are detected using one or more machine learning algorithms including a uniform manifold approximation and projection (UMAP) algorithm.

19. The computerized decision support system of claim 17, wherein the asynchronies are detected using a uniform manifold approximation and projection (UMAP) model.

20. The computerized decision support system of claim 17, wherein the intervening action comprises automatically adjusting, by the one or more hardware processors, one or more ventilator settings associated with the patient based on a type of asynchrony associated with the one or more asynchronies.

21. The computerized decision support system of claim 17, wherein detecting the one or more asynchronies comprises applying a set of heuristic rules to the plurality of features for each breath to determine one or more anomaly groups that represent at least one asynchrony.

22. The computerized decision support system of claim 17, wherein the operations further comprise, based on the plurality of features for each breath, further detecting one or more instances of leakage.

23. The computerized decision support system of claim 17, wherein the operations further comprise:
applying a first machine-learning electronic model of a first type, to information associated with the plurality of measurements, to select features for a potential feature pool;
applying a second machine-learning electronic model of a second type, to information associated with the potential feature pool, to select one or more final feature sets; and
applying a third type of machine-learning electronic model of a third type, to information associated with the one or more final feature sets, to generate a prediction indicative of the one or more asynchronies.

24. The computerized decision support system of claim 23, wherein: the first type corresponds to a gradient boosted tree model, the second type corresponds to an adaptive GLMnet, and the third type corresponds to a generalized linear model.

25. A computerized method for detecting patient ventilator asynchrony, the computerized method comprising:
receiving a plurality of measurements taken by a ventilator associated with a patient, the plurality of measurements being acquired over a time span;
constructing one or more time series from the plurality of measurements for the ventilator to detect:
(a) a plurality of peak measurement values using at least one of the one or more time series; and
(b) a plurality of breaths of the patient corresponding to the plurality of peak measurement values;
for each breath of the plurality of breaths, computing via one or more hardware processors a plurality of features based on the plurality of measurements, the plurality of features selected from a group comprising at least:
a flow ratio calculated from a ratio of exhalation volume and inhalation volume within an individual breath;
a volume oscillation ratio calculated from a ratio of a maximum volume oscillation and an in volume within an individual breath, wherein the maximum volume oscillation is calculated from a difference of minimum and maximum volume during a time when a volume is at least 70% of a maximum volume within an individual breath;
a volume peak time ratio calculated from a ratio between a volume peak time to next and a volume peak time to previous, wherein the volume peak time to next is calculated from a distance between a current breath's peak to the next breath's peak and the volume peak time to previous is calculated from a distance between the current breath's peak to a previous breath's peak;
a pressure peak time ratio calculated from a ratio between a pressure peak time to next and a pressure peak time to previous, wherein the pressure peak time to next is calculated from the time between a first peak of one breath to a first peak of a next breath and the pressure peak time to previous is calculated from the time between the first peak of one breath and a first peak in a previous breath; and
a time ratio calculated from a ratio of in time and out time within an individual breath;
detecting one or more asynchronies between the patient and the ventilator responsive to determining that the plurality of features correspond to one or more phenomena from a group comprising at least:
a flow ratio less than 0.6;
a volume oscillation ratio greater than 0.25;
a volume peak time ratio less than 0.7;
a pressure peak time ratio less than 0.6; and
a time ratio less than 0.8; and
responsive to detecting the one or more asynchronies:
automatically initiating an intervening action,
wherein:
the intervening action comprises adjusting via the one or more hardware processors at least one of flow, volume, or pressure of the ventilator, and
the intervening action facilitates at least one effect from a group comprising:
reducing a detected presence of the one or more asynchronies;
reducing an adverse effect associated with the one or more asynchronies;
countering the detected presence of the one or more asynchronies; and
countering the adverse effect associated with the one or more asynchronies.

26. The computerized method of claim 25, wherein detecting the one or more asynchronies is based further on a semi-supervised machine-learning electronic model.

27. The computerized method of claim 26, wherein the semi-supervised machine-learning electronic model is trained using a plurality of hand-labeled samples as ground truth data.

28. The computerized method of claim 25, wherein the intervening action reduces the detected presence of the one or more asynchronies.

29. The computerized method of claim 25, wherein the intervening action is initiated based at least on a first asynchrony of the one or more asynchronies, and further comprising after automatically initiating the intervening action:
detecting a second asynchrony in an additional breath based on additional measurements taken by the ventilator after the plurality of measurements; and
based on the second asynchrony, initiating a second intervening action.

30. The computerized method of claim 29, wherein the second intervening action reduces a detected presence of the second asynchrony.

31. The computerized method of claim 25, further comprising:
performing a first ventilator adjustment, in response to the automatic initiating, based on the plurality of measurements; and performing a second ventilator adjustment, after the first ventilator adjustment, based on additional measurements taken by the ventilator after the plurality of measurements.

\* \* \* \* \*